US00PP11985P2

(12) United States Plant Patent
Littlejohn

(10) Patent No.: US PP11,985 P2
(45) Date of Patent: Jul. 10, 2001

(54) ORNITHOGALUM PLANT NAMED 'TIPPER'

(75) Inventor: Gail Littlejohn, Joostenbergvlakte (ZA)

(73) Assignee: ARC Roodeplatt (Western Cape) (ZA)

( * ) Notice: Subject to any disclaimer, the term of this patent is extended or adjusted under 35 U.S.C. 154(b) by 0 days.

(21) Appl. No.: 09/163,361

(22) Filed: Sep. 30, 1998

(51) Int. Cl.[7] ..... A01H 5/00
(52) U.S. Cl. ..... Plt./263
(58) Field of Search ..... Plt./263

(56) References Cited

PUBLICATIONS

UPOV–ROM GITIM JOUVE computer database 1999/02; citation for 'Tipper', Mar. 1999.*

* cited by examiner

*Primary Examiner*—Bruce R. Campell
*Assistant Examiner*—Wendy C. Baker
(74) *Attorney, Agent, or Firm*—Foley & Lardner

(57) ABSTRACT

A new and distinct cultivar of *Ornithogalum thyrosides* named 'Tipper', characterized by its creamy white tepal color with black coloring near ovary; leaf color of 137A RHS; lanceolate leaf shape and flat growing leaves.

1 Drawing Sheet

The present invention comprises a new and distinctive cultivar of Ornithogalum, botanically known as *O thyrosides* and hereinafter referred to by the cultivar name 'Tipper'. The genus Ornithogalum contains approximately 100 species of bulbous perennials native to Africa, Europe, and Western Asia. Most members of the genus are winter- and spring-flowering.

Under natural conditions, 'Tipper' grows during the autumn and winter and flowers in the spring. The cultivar has a short dormant phase in summer. 'Tipper' is easily propagated in vitro with leaf cuttings. Most importantly, 'Tipper' is easily grown in pots and easily cultivated in the field. The leaves emerge erect from the bulb but bend towards the ground as the leaves mature and grow longer in length.

BACKGROUND OF THE INVENTION

'Tipper' is a product of a planned breeding program which had the objective of creating new Ornithogalum cultivars to expand the characteristics of cultivars available in the marketplace. 'Tipper' was originated from a hybridization made by the inventor in a controlled breeding program in ARC Fijnbos Unit, Private Bag X1, 7607 Elzenburg RSA in October 1994. The female and male parents were proprietary selections of *O. thyrosides*. 'Tipper' was discovered and selected as one flowering plant within the progeny of the stated cross by Gail Littlejohn on November 1995 in a controlled environment in ARC Fijnbox, Elzenburg, South Africa.

The first act of asexual reproduction of 'Tipper' was accomplished by in vitro propagation in December 1995 in a controlled environment in ARC Roodeplaat (Western Cape), Mudersvlei Road, Elsenburg, South Africa.

Horticultural examination of selected units initiated in December 1995 has demonstrated that the combination of characteristics as herein disclosed for 'Tipper' are firmly fixed and are retained through successive generations of asexual reproduction.

'Tipper' has not been observed under all possible environmental conditions. The phenotype may vary significantly with variations in environment, such as temperature, light intensity, and day length, without, however, variance in genotype. The following observations, measurements, and comparisons describe plants grown in ARC Fijnbox, Elzenburg, South Africa under conditions which approximate those generally used in commercial practice.

The following traits have been repeatedly observed and are determined to be basic characteristics of 'Tipper' which, in combination, distinguish this Ornithogalum as a new and distinct cultivar.

BRIEF SUMMARY OF THE INVENTION

'Tipper' is particularly characterized by the following characteristics.

1. Creamy white tepal color with black coloring near ovary;
2. Leaf color of 137A RHS;
3. Lanceolate leaf shape; and
4. Flat growing leaves.

BRIEF DESCRIPTION OF THE DRAWINGS

The accompanying photographic illustration shows typical plant and flower characteristics of 'Tipper', with colors being as true as possible with illustrations of this type.

DETAILED BOTANICAL DESCRIPTION

Figure 1:
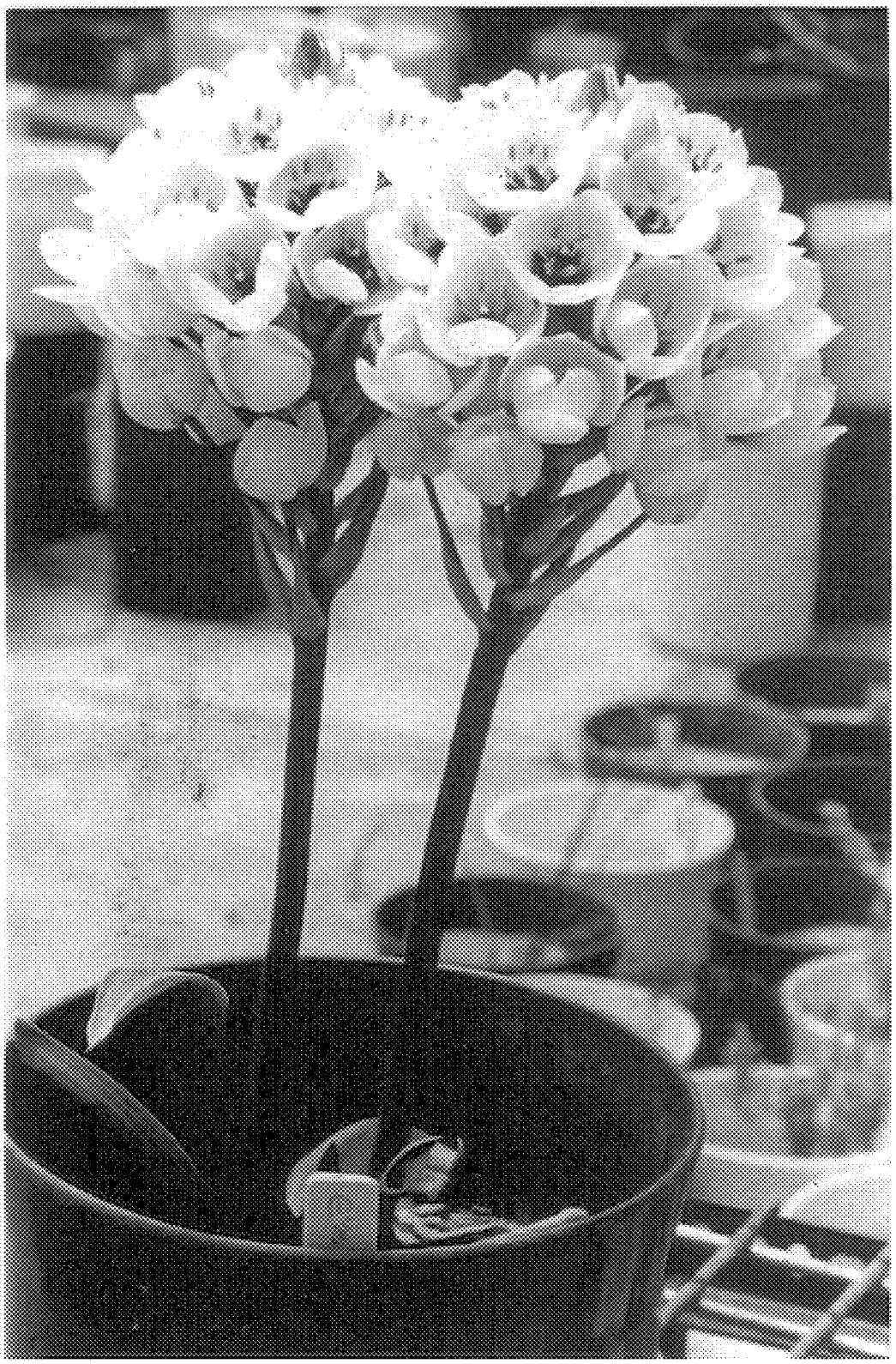
FIG. 1 is a side view showing the inflorescence, stem and leaves flower characteristics of 'Tipper'. In the following description, color references are mate to The Royal Horticultural Society Colour Chart (R.H.S.). The color values were determined between 11:00 a.m. and 12:00 p.m. in Elzenburg, South Africa.

The following traits have been repeatedly observed and, in combination, distinguish 'Tipper' as a new and distinct cultivar. These observations, measurements and descriptions were taken for 'Tipper' grown under greenhouse conditions which were approximately those generally used in commercial practice:

ORIGIN

Parentage:

*Female parent.*—Proprietary selection of *O. thyrosides.*
*Male parent.*—Proprietary selection of *O. thyrosides.*

Classification:

*Botanical.—Ornithogalum thyrosides.*

Plant:

*Height.*—Approximately 40 cm with a leaf length of 202 mm from full flowering size bulbs obtained after about two years of cultivation in a greenhouse in Elsenberg, South Africa.

*Stems.*—Length 9without inflorescence): approx. 400 mm. Diameter: approx. 12 mm.

*Foliage.*—Quantity: Approximately 9. Size of leaf: 21–33 mm wide, 250–350 mm long. Shape of leaf: Lanceolate. Margin: Smooth. Color: Upper surface: Dark-green, RHS 137B to RHS 137C. Lower surface: RHS 137C.

*Bulb.*—Size: Round to oblate, approximately 22 mm in diameter. Color: White, RHS 155D; cream to RHS 155D, covered with one or two dry scale layers that are cream to light-brown, RHS 161C.

Inflorescence:

*Organization.*—Corymbose raceme with approx. 38 flowers within which blooms are contained.

*Size.*—Approximately 185 mm in length.

Flower:

*Shape.*—Single flower with a cup-shape.

*Size.*—Approximately 34.8 mm in diameter.

*Tepal.*—Length: Approx. 25–30 mm. Width: Approx. 15–20 mm. Shape: Oval. Color: Creamy white changing to a yellow line to a black/green center near ovary. Number: 6. Duration of bloom: Approximately 6 weeks. Lastingness of individual bloom: Approximately 2 weeks.

*Fragrance.*—None.

Reproductive organs:

*Stamens.*—Color: White. No. of stamens: 6.

Styles:

*Ovaries.*—Number: 1. Color: White but black toward ovary.

*Seed/Fruit.*—Seed capsules are only formed when deliberately pollinated by hand since flowers are sterile when pollinated by their own pollen. Seeds are approximately 1–2 mm in length, black and angular in shape. The seed capsules are initially black drying to a yellow-brown color, RHS 160A, before the seed is released. The capsule is approximately 15 mm in length.

*Cold/heat tolerance.*—At temperatures below freezing, the leaves become damaged. At high temperatures, the leaves die since the plant remains dormant in the natural habitat during hot, summer months.

*Resistance/susceptibility to disease.*—Very susceptible to Ornithogalum mosaic virus; some problems with Erwinia and Helminthosporium spp. can be expected.

1. A new and distinct cultivar of *Ornithogalum thyrosides* plant named 'Tipper' as illustrated and described.

* * * * *